United States Patent [19]

Buckle

[11] Patent Number: 4,732,901

[45] Date of Patent: Mar. 22, 1988

[54] CERTAIN PYRIDYL, THIENYL OR FURYL PROPENOIC ACIDS OR ESTERS HAVING ANTI-INFLAMMATORY ANTI-ALLERGIC PROPERTIES

[75] Inventor: Derek R. Buckle, Redhill, England

[73] Assignee: Beecham Group p.l.c., England

[21] Appl. No.: 834,317

[22] Filed: Feb. 27, 1986

[30] Foreign Application Priority Data

Mar. 1, 1985 [GB] United Kingdom ............... 8505285

[51] Int. Cl.$^4$ ................. C07D 213/55; C07D 307/54; C07D 333/24; A61K 31/44
[52] U.S. Cl. ................................. 514/277; 514/438; 514/461; 549/79; 549/499; 546/341; 544/335; 544/336; 548/170; 548/235; 548/247; 548/255; 548/262; 548/342; 548/378; 548/562
[58] Field of Search ............... 546/341; 549/79, 499; 514/277, 438, 461

[56] References Cited

U.S. PATENT DOCUMENTS 4,501,893 2/1985 Findlay et al. ..................... 546/281

*Primary Examiner*—Alan L. Rotman
*Attorney, Agent, or Firm*—Jacobs & Jacobs

[57] ABSTRACT

Compounds of formula (I):

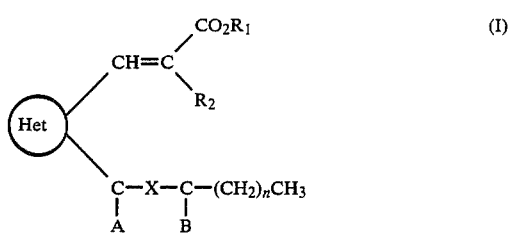

in which
$R_1$ is hydrogen or $C_{1-6}$ alkyl;
$R_2$ is hydrogen or a group —$CO_2R_3$ where $R_3$ is hydrogen or $C_{1-6}$ alkyl;
n is an integer of from 2 to 12;
X represents a double or triple bond, and each of A and B represents hydrogen when X is a double bond, or both A and B are absent when X is a triple bond; and Het represents an aromatic heterocyclic ring, are disclosed as inhibitors of 5-lipoxygenase.

12 Claims, No Drawings

CERTAIN PYRIDYL, THIENYL OR FURYL PROPENOIC ACIDS OR ESTERS HAVING ANTI-INFLAMMATORY ANTI-ALLERGIC PROPERTIES

This invention relates to novel aromatic heterocyclic carboxylic acid derivatives, to processes for preparing them, to pharmaceutical compositions containing them and their use in medicine.

It is known that certain arachidonic acid metabolites can produce harmful effects in man. For example, some prostaglandins and thromboxanes, produced via cyclooxygenation of arachidonic acid, can contribute to inflammation in such diseases as rheumatoid arthritis, and that products produced via lipoxygenation of arachidonic acid, such as the leukotrienes, are implicated in the production of the pathology of asthma and other allergic diseases.

European Published Patent Application No. 0109225 discloses certain aromatic carboxylic acid derivatives which can inhibit arachidonic acid metabolism by one or both of these metabolic pathways.

We have now discovered a new class of aromatic heterocyclic carboxylic acid derivatives which can similarly inhibit arachidonic acid metabolism and are thus of value in the prophylaxis and treatment of diseases whose symptoms are controlled by these mediators.

According to the present invention there is provided a compound of formula (I):

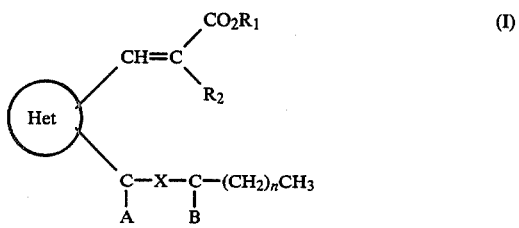

in which
$R_1$ is hydrogen or $C_{1-6}$ alkyl;
$R_2$ is hydrogen or a group $-CO_2R_3$ where $R_3$ is hydrogen or $C_{1-6}$ alkyl;
n is an integer of from 2 to 12;
X represents a double or triple bond, and each of A and B represents hydrogen when X is a double bond, or both A and B are absent when X is a triple bond; and

represents an aromatic heterocyclic ring.
When X is a double bond, the hydrocarbon chain containing X may have the (E) or (Z) absolute configuration, preferably (Z).

Similarly, the group

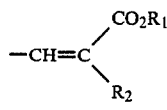

may have the (E) or (Z) absolute configuration about the double bond.

The compounds of this invention can exist, therefore, in up to four geometric isomeric forms, and the invention encompasses all geometric isomers of the compounds of formula (I) whether as individual isomers or admixed with each other in any proportion.

Suitably the aromatic heterocyclic ring comprises from 4 to 7 ring atoms up to 4 of which are heteroatoms selected from oxygen, nitrogen and sulphur.

Examples of suitable aromatic heterocyclic groups include furan, thiophene, pyridine, pyrrole and isoxazole, oxazole, imidazole, thiazole, pyrazole, triazole, pyrazine, pyrimidine.

The heterocyclic aromatic ring may be substituted 1,2; 1,3; or 1,4 with respect to each other, preferably 1,2 and 1,3, and most preferably 1,2.

Preferably, n is an integer of from 4 to 12.

When compounds of formula (I) form salts, such as metal salts, or solvates, such as hydrates these also form part of this invention.

The compounds of formula I or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula I or its salt or solvate.

One preferred pharmaceutically acceptable form is the crystalline form, including such form in a pharmaceutical composition. In the case of salts and solvates the additional ionic and solvent moieties must also be non-toxic.

Salts of compounds of formula (I) need not be pharmaceutically acceptable, since they can be used as intermediates to prepare other pharmaceutically acceptable compounds of the invention.

Examples of pharmaceutically acceptable salts include alkali metal and alkaline earth metal salts, such as sodium, potassium and magnesium salts,; and salts with ammonia, organic bases and amino compounds.

Examples of compounds of formula (I) include
(E) 3-[3-(1-tridecynyl)-4-pyridyl]prop-2-enoic acid;
(E) 3-[3-(1-tridecynyl)-2-furanyl]prop-2-enoic acid;
2-[3-(1-tridecynyl)-4-pyridyl]methylenepropan-, 3-dioic acid; (E-)3-[5-(1-Octynyl)-2-furanyl]prop-2-enoic acid;
2-[5-(1-octynyl)-2-furanylmethylene]propan-1, 3-dioic acid,
(Z)-2-[5-(1-octynyl)-2-furanylmethylene]propan-1, 3-dioic acid;
2-[(Z)-5-(1-octenyl)-2-furanylmethylene]propan-1,3-)dioic acid;
(Z)-2-[(Z)-5-(1-octenyl)-2-furanylmethylene]propan-1, 3-dioic acid.
(E)-3-[3-(1-Octynyl)-2-furanyl]prop-2-enoic acid;
2-[3-(1-octynyl)-2-furanylmethylene]propan-1, 3-dioic acid;
(Z)-2-[3-(1-Octynyl)-2-furanylmethylene]propan-1, 3-dioic acid;
2-[(Z)-3-(1-Octenyl)-2-furanylmethylene]propan -1, 3-dioic acid;

(Z)-2-[(Z)-3-(1-Octenyl)-2-furanylmethylene]propan-1, 3-dioic acid;
(E)-3-[5-(1-Octynyl)-2-thienyl]prop-2-enoic acid;
2-[5-(1-octynyl)-2-thienylmethylene]propan-1, 3-dioic acid;
(Z)-2-[5-(1-Octynyl)-2-thienylmethylene]propan-1, 3-dioic acid;
2-[5-(1-Octynyl)-2-thiophenylmethylene]propan-1, 3-dioic acid;
(E)-3-[4-(1-Octynyl)-2-thienyl]prop-2-enoic acid;
(E)-3-[4-(1-Octynyl)-3-thienyl]prop-2-enoic acid;
3-[2-(1-Octynyl)-3-thiophene]prop-2-enoic acid; and salts and $C_{1-6}$ alkyl esters thereof.

According to a further aspect of the present invention there is provided a process for preparing a compound of formula (I) which comprises providing a compound of formula (X)

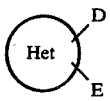  (X)

in which

is as defined for formula (I);
D is CHO or Z where Z is

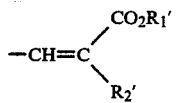

where $R_{1'}$ and $R_{2'}$ are $R_1$ and $R_2$ as defined for formula (I) provided that $R_1$ and $R_3$ are not hydrogen, and E is Y where Y is a halogen, or W where W is

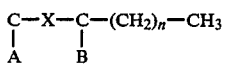

where X, A, B, and n are as defined for formula (I), and when D is CHO and E is W reacting the compound of formula (X) with a compound of formula (III)

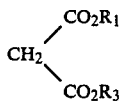  (III)

in which $R_1$ and $R_3$ are as defined for formula (I) or with a compound of formula (VII) $R_4R_5R_6P=CHCO_2R_1$ (VII) in which $R_4$, $R_5$, $R_6$ are each independently a $C_{1-6}$ alkyl or an aryl group, and when D is Z and E is Y reacting the compound of formula (X) with a compound of formula (V)

$$CH_3(CH_2)_nC\equiv CH \quad (V)$$

to obtain a compound of formula (I), and thereafter if desired carrying out one or more of the following steps:
 (i) converting a group $R_1$ to a different group $R_1$,
 (ii) converting a group $CO_2R_3$ to a different group $R_2$ (iii) reducing a triple bond X to a double bond.

More specifically the invention provides a process for preparing a compound of formula (I) thereof which process comprises reacting a compound of formula (II),

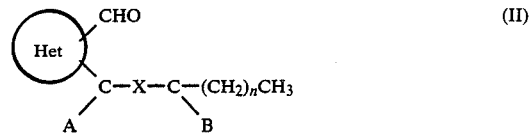  (II)

wherein Het, A, B, X, and n are as defined in relation to formula (I), with a compound of formula (III)

  (III)

wherein $R_1$ and $R_3$ are as defined in relation to formula (I), and thereafter if desired carrying out one or more of the following steps:
 (i) converting one group $R_1$ to another such group;
 (ii) converting a group $CO_2R_3$ to a different $R_2$ group;
 (iii) where X is a triple bond, reducing it to a double bond.

The reaction between the compound of formula (II) and the compound of formula (III) wherein $R_1$ and/or $R_3$ are other than hydrogen is suitably carried out in an inert organic solvent such as benzene or toluene under reflux in the presence of a catalyst under conditions of azeotropic water removal. A suitable catalyst is piperidine benzoate.

When the compound of formula (III) employed in the reaction is malonic acid (i.e. both $R_1$ and $R_3$ are hydrogen), compounds of formula (I) wherein $R_1$ and $R_2$ are hydrogen can be obtained directly by heating the reactants under reflux in an organic solvent such as pyridine and in the presence of a basic catalyst such as piperidine.

When the resultant compound of the invention formed by reacting compounds of formula (II) and (III) includes a carbon-carbon triple bond, as will occur when

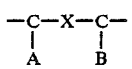

is —C≡C—, a further compound of the invention may be formed by reducing the triple bond to a double bond. This reduction may be carried out by conventional literature procedures, preferably by hydrogenation in the presence of a Lindlar catalyst, or other poisoned catalyst such as palladium on barium sulphate. This reduction tends to be stereospecific to the extent that the $-X-(CH_2)_nCH_3$ chain in the resultant compound of the invention has the (Z) configuration.

Compounds of the invention in which each of $R_1$ and $R_3$ are $C_{1-6}$ may be quantitatively hydrolysed with base, for example lithium hydroxide in aqueous tetrahydrofuran, to give a mono- or dibasic acid of formula (I), in which only one of $R_1$ and $R_3$ is hydrogen, or both of $R_1$ and $R_3$ are hydrogen, respectively. In general, treatment with 1 mole equivalent of base will yield a monobasic acid, and 2 or more mole equivalents will yield a dibasic acid.

The monobasic acids of formula (I) may have different geometric isomerism, according to whether $R_1$ or $R_3$ is hydrogen.

Compounds of formula (I) wherein $R_1$ and $R_3$ are $C_{1-6}$ alkyl can be obtained from compounds of formula (I) wherein $R_1$ and $R_3$ are hydrogen by conventional esterification techniques.

Compounds of formula (II) can be prepared by reacting a compound of formula (IV)

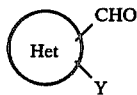  (IV)

where

is as defined in relation to formula (I) and Y is a halogen, such as bromine or iodine; with a compound of formula V

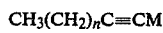

where M is hydrogen or a metal, and n is as defined in relation to formula (I), in the presence of a catalyst.

Suitably the catalyst is a palladium catalyst, in particular a palladium (II) source solubilised by a triarylphosphine such as triphenyl phosphine or tri(o-tolyl) phosphine. The catalytic species in this case is believed to be Pd°.

When M is hydrogen, the reaction is carried out in an organic solvent such as a tertiary amine for example triethylamine, under an inert atmosphere such as performed at an elevated temperature of from 50°–150° C., under reflux. Under these conditions the reaction may proceed for 2 to 48 hours. Usually about 24 hours, suitably until some precipitation of trialkylamine hydrohalide occurs. The reaction may also be monitored using hplc or other related techniques.

When M is a metal it is preferably zinc and the reaction is carried out in an organic solvent such as tetrahydrofuran, at 20° to 80° C.

Compound of formula (III) (IV) and (V) are either known compounds or can be prepared from known compounds by known methods.

The present invention also provides a process for preparing a compound of formula (I) which process comprises reacting a compound of formula (VI)

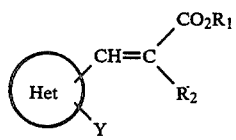  (VI)

wherein

, $R_1$ and $R_2$ are as defined in relation to formula (I) provided that $R_1$ and $R_3$ are not hydrogen, and Y is as defined in relation to formula (IV); with a compound of formula (V) as hereinbefore defined; and thereafter if desired carrying out one or more of the following steps:
  (i) converting one group $R_1$ to another such group;
  (ii) converting a group $CO_2R_3$ to a different $R_2$ group;
  (iii) reducing the triple bond to a double bond.

Suitable reaction conditions are those described above for the reaction between compounds of formula (IV) and (V).

Compounds of formula (VI) above can be prepared by reacting a compound of formula (IV) as defined above with a compound of formula (III) as defined above, under conditions similar to those described for the reaction of a compound of formula (II) with a compound of formula (III), and esterifying where necessary.

The present invention further provides a process for preparing a compound of formula (I) wherein $R_2$ is hydrogen; which process comprises reacting a compound of formula (II) as defined above with a compound of formula (VII)

  (VII)

wherein $R_1$ is as defined in relation to formula (I) and $R_4$, $R_5$ and $R_6$ are each independently a $C_{1-6}$alkyl or an aryl group such as phenyl and thereafter if desired carrying out one or more of the following steps:
  (i) converting one group $R_1$ to another such group;
  (ii) where X is a triple bond, reducing it to double bond.

The reaction is suitably carried out in an inert organic solvent such as diethylether, tetrahydrofuran, ethanol, benzene, toluene, dimethylformamide or dimethylsulphoxide at a temperature of from 20°–200° C.

The reaction is suitably carried out under an inert atmosphere of for example nitrogen.

Compounds of formula (VII) are either known compounds or are suitably generated by reaction of a compound of formula (VIII)

  (VIII)

wherein $R_1$ is as defined in relation to formula (I), $R_4$, $R_5$ and $R_6$ are as defined in relation to formula (VII) and $Y^1$ is halogen such as bromine or iodine; with a strong base.

Examples of suitable bases include alkali metal $C_{1-6}$ alkoxides such as sodium methoxide, sodium ethoxide, potassium butoxide or lithium ethoxide, or alkali metal hydroxides such as sodium hydroxide.

Compounds of formula (VIII) are known compounds or can be produced from known compounds by known methods.

The compounds of formula (I) we indicated as active therapeutic agents by their inhibition of 5-lipoxygenase and cyclooxygenase.

Accordingly the present invention also provides a pharmaceutically acceptable compound of the formula (I), or a pharmaceutically acceptable salt or solvate thereof, for use in treatment of the human or animal body, particularly for the treatment or prophylaxis of allergic diseases, such as asthma, hayfever, rhinitis or allergic eczema, or for treatment of inflammatory conditions such as arthritis and psoriasis.

The present invention also provides a pharmaceutical composition comprising a pharmaceutically acceptable compound of the formula (I), or a pharmaceutically acceptable salt or solvate thereof, in admixture or conjunction with a pharmaceutically acceptable carrier.

Preferably, a pharmaceutical composition of the invention is in unit dosage form and in a form adapted for use in the medical or veterinarial fields. For example, such preparations may be in a pack form accompanied by written or printed instructions for use as an agent in the treatment or prophylaxis of any of the disorders mentioned above.

The suitable dosage range for the compounds of the invention may vary from compound to compound and may depend on the condition to be treated. It will also depend, inter alia, upon the relation of potency to absorbability and the mode of administration chosen. The compound or composition of the invention may be formulated for administration by any route, the preferred route depending upon the disorder for which treatment is required, and is preferably in unit dosage form or in a form that a human patient may administer to himself in a single dosage. Advantageously, the composition is suitable for oral, rectal, topical, parenteral, intravenous or intramuscular administration or through the respiratory tract. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories. Compositions which are especially suitable for administration to the respiratory tract and for topical administration are discussed in more detail below.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmacetucially acceptable setting agents such as sodium lauryl sulphate.

Solid compositions may be obtained by conventional methods of blending, filling tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository or for presentation in an injectable form in an aqueous or non-aqueous solution, suspension or emulsion in a pharmaceutically acceptable liquid, e.g. sterile pyrogen-free water or a parenterally acceptable oil or a mixture of liquids, which may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

Compositions of this invention may also suitably be presented for administration to the respiratory tract as a snuff or an aerosol or solution for a nebulizer, or as a microfine powder for insufflation, alone or in combination with an inert carrier such as lactose. In such a case the particles of active compound suitably have diameters of less then 50 microns, preferably less than 10 microns. Where appropriate, small amounts of other anti-asthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

For topical administration, compositions may be presented as an ointment, cream, lotion, gel, gel stick, spray, aerosol, or skin paint.

By way of example, in any of the preceding formulations a suitable dosage unit might contain 0.01 to 500 mgs of active ingredient, more suitably 1 to 500 mgs via the oral route, 0.01 to 10 mgs via inhalation. The effective dose of compound depends on the particular compound employed, the condition of the patient and on the frequency and route of administration, but in general is in the range of from 0.001 mg/kg/day to 100 mg/kg/day inclusive of the patient's body weight. For use in treatment of inflammatory disorders a composition of the invention will preferably be in a form suitable for oral administration, for example a tablet or capsule or a sachet containing reconstitutable powder. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

Within the above mentioned dosage ranges, no adverse toxicological effects are indicated with the compounds of the invention.

The present invention also provides a method for treating allergic diseases or inflammatory conditions in human or non-human animals which comprises administering to the sufferer an effective non-toxic amount of a compound according to formula (I) or a pharmaceutically acceptable salt or solvate thereof.

Also included in the present invention is the use of a compound of formula (I), or a pharmaceutically acceptable salt or solvate thereof, in the manufacture of a medicament for treatment of the above disorders.

Compounds of this invention, their preparation and their biological activity are illustrated in the following Examples and Pharmacological Data.

EXAMPLE 1

3-(1-Tridecynyl)pyridine-4-carboxaldehyde

Palladium acetate (10.8 mg) was added to a stirred, deaerated solution of 3-bromopyridine-4-carboxaldehyde (0.80 g, 4.5 mmole; prepared as described by E. J. Corey, S. G. Pyne and A. I. Schafer, Tet. Letters, 3291, 1983), 1-tridecyne (1.4 g) and triphenylphosphine (36 mg) in anhydrous triethylamine (18 ml) maintained under an atmosphere of nitrogen. The mixture was stirred at 105° C. for 19 hours after which time it was cooled and the precipitated triethylamine hydrobromide filtered off. Chromatography of the evaporated filtrate on silica using dichloromethane as eluant afforded 0.93 g (73%) of the title compound as a white crystalline solid of mp (petroleum ether [bp. 40°-60° C.]) 38°-39° C., $\nu_{max}$ (mull) 2230, 1710 cm$^{-1}$; $\delta$(CDCl$_3$) 0.87 (3H, distorted t, terminal CH$_3$), 1.12–1.76 (18H, m, alkylene chain), 2.48 (2H, t, J 6 Hz, CH$_2$—C≡C), 7.62 (1H, d, J 5 Hz, C-5H), 8.63 (1H, d, J 5 Hz, C-6H), 8.82 (1H, s, C-2H), 10.52 (1H, s, aldehyde C-H).

Found; C, 79.62; H, 9.45; N, 5.04; C$_{19}$H$_{27}$NO. requires; C, 79.95; H, 9.53; N, 4.91%.

EXAMPLE 2

3-[3-(1-Tridecynyl)-4-pyridyl]prop-2-enoic acid

Piperidine (0.1 ml) was added to a stirred, homogeneous mixture of 3-(1-tridecynyl)pyridine-4-carboxaldehyde (0.73 g, 2.56 mmole, from Example 1), malonic acid (523 mg, 5.12 mmole) and pyridine (5 ml) under nitrogen and the mixture was heated to 80° C. for 1 hour. After then refluxing for an additional 3 hours the mixture was cooled, added to water (40 ml) and acidified to pH 1. The resulting precipitate was washed with water, dried and recrystallised from methanol to give 0.48 g (57%) of the title compound, mp 177°–178° C., $\nu_{max}$ (mull) 2450 (broad), 1870 (broad), 1690, 1625, 1595 cm$^{-1}$; $\delta$(DMSO) 0.84 (3H, distorted t, terminal CH$_3$), 1.23 (14H, m, alkylene chain), 1.45 (2H, m, CH$_2$(CH$_2$)$_2$C≡C), 1.59 (2H, m, CH$_2$CH$_2$C≡C), 2.54 (2H, t, J 6.6 Hz, CH$_2$C≡C), 6.88 (1H, d, J 16 Hz, C═CHCO), 7.82 (1H, d, J 5 Hz, C-5H), 7.83 (1H, d, J 16 Hz, Ar CH═C), 8.52 (1H, d, J 5 Hz, C-6H), 8.64 (1H, s, C-2H), 12.81 (1H, s, OH).

Found; C, 77.11; H, 8.95; N, 4.45; C$_{21}$H$_{29}$NO$_2$. requires; C, 77.02; H, 8.93; N, 4.28%.

EXAMPLE 3

Diethyl 2-[3-(1-tridecynyl)-4-pyridyl]methylenepropan-1,3-dioate

A mixture of 3-(1-tridecynyl)pyridine-4-carboxaldehyde (7.13 g, 25 mmole, from Example 1), diethyl malonate (4.12 g), benzoic acid (0.145 g) and piperidine (0.18 ml) in benzene (45 ml) was refluxed under conditions of water removal for 24 hours. After cooling, ether was added and the solution was washed with dilute sodium bicarbonate solution and dried. Evaporation and distillation of excess diethyl malonate under reduced pressure afforded an oil which on silica gel chromatography gave 4.90 g (46%) of the title compound as a pale yellow oil, bp$_{0.1}$ 250° C. (Kugelrohr), $\nu_{max}$ (film) 2930, 2850, 2220, 1730, 1640, 1250, 1215 cm$^{-1}$; $\delta$(CDCl$_3$) 0.83 (3H, distorted t, terminal CH$_3$), 1.12–1.65 (24H, m, ester CH$_3$+alkylene envelope), 2.43 (2H, t, J 6 Hz, CH$_2$C≡C), 4.22 (2H, q, J 7 Hz, ester CH$_2$), 4.30 (2H, q, J 7 Hz, ester CH$_2$), 7.25 (1H, d, J 5 Hz, C-5H), 7.99 (1H, s, CH═C), 8.42 (1H, d, J 5 Hz, C-6H), 8.63 (1H, s, C-2H).

Found; C, 72.77; H, 8.53; N, 3.35; C$_{26}$H$_{37}$NO$_4$. requires; C, 73.03; H, 8.72; N, 3.28%.

EXAMPLE 4

2-[3-(1-Tridecynyl)-4-pyridyl]methylenepropane-1,3-dioic acid

Diethyl 2-[3-(1-tridecynyl)-4-pyridyl]methylenepropane-1,3-dioate (0.47 g, 1.1 mmole, from Example 3) was added to a solution of potassium hydroxide (0.66 g) in water (7.5 ml) and the mixture was heated to reflux for 24 hours. The resulting clear solution was then acidified at 0° C. and the precipitated product was filtered off and washed with water. Recrystallisation of the dried material from ethyl acetate gave 1.37 g (34%) of the title compound, mp 175°–177° C., $\nu_{max}$ (mull) 2500 (broad), 1740 cm$^{-1}$; $\delta$(DMSO) 0.84 (3H, distorted t, terminal CH$_3$), 1.20 (14H, m, alkylene chain), 1.42 (2H, m, CH$_2$(CH$_2$)$_2$C≡C), 1.57 (2H, m, CH$_2$CH$_2$C≡C), 2.50 (2H, t, CH$_2$C≡C), 7.41 (2H, d, J 5.1 Hz, C-5H), 7.74 (1H, s, Ar CH═C), 8.56 (1H, d, J 5.1 Hz, C-6H), 8.67 (1H, d, J 0.5 Hz, C-2H), 13.73 (2H, broad exchangeable, CO$_2$H).

Found; C, 71.70; H, 8.07; N, 3.83; C$_{22}$H$_{29}$NO$_4$. requires; C, 71.13; H, 7.87; N, 3.77%.

EXAMPLE 5

3-Bromofuran-2-carboxaldehyde

3-Bromofuran (7.3 g, 50 mmole) was added to a solution of lithium isopropylamide (from diisopropylamine [5.1 g, 50 mmole] and n-butyl lithium [33.5 ml of 1.5M solution in hexane]) in dry tetrahydrofuran (50 ml) at −80° C. under nitrogen and the mixture was stirred at this temperature for a further 150 minutes. Dry N,N-dimethylformamide (3 equiv, 11.0 g, 150 mmole) was added and after a further 1 hour at this temperature the reaction mixtue was allowed to attain ambient temperature over 1 hour. Water and ether were added and the phases separated. Evaporation of the dried organic phase gave a red oil which on chromatography with dichloromethane on silica gave 7.55 g (87%) of the product as a pale yellow solid, $\nu_{max}$ (mull) 3140, 3120, 1650 (broad), 1545, 1475, 1385, 1360, 1275 cm$^{-1}$; $\delta$(CDCl$_3$) 6.67 (1H, d, J ca 1.5 Hz, C-4H), 7.65 (1H, d, J ca 1.5 Hz, C-5H), 9.79 (1H, s, CHO).

EXAMPLE 6

3-(1-Tridecynyl)furan-2-carboxaldehyde

Reaction of 3-bromofuran-2-carboxaldehyde (3.86 g, 21.5 mmole, from Example 5) with 1-tridecyne (6.7 g) as described in Example 1 afforded 2.28 g (39% of the title compound after chromatography with dichloromethane on silica. Recrystallisation from petroleum ether [bp 40°-60° C.] afforded material of mp 56°–57° C., $\nu_{max}$ 3170, 3120, 2230, 1660, 1420, 1355, 1280 cm$^{-1}$; δ(CDCl$_3$) 0.84 (3H, distorted t, terminal CH$_3$), 1.11–1.67 (18H, m, alkylene chain), 2.40 (2H, t, J 6.3 Hz, CH$_2$C≡C), 6.47 (1H, d, J ca 2 Hz, C-4H), 7.51 (1H, d, J ca 2 Hz, C-5H), 9.71 (1H, s CHO).

Found; C, 78.47; H, 9.70; C$_{18}$H$_{26}$O$_2$. requires; C, 77.79; H, 9.55%.

EXAMPLE 7

3-[3-(1-Tridecynyl)-2-furanyl]prop-2-enoic acid

Reaction of 3-(1-tridecynyl)furan-2-carboxaldehyde (700 mg, 2.56 mmole from Example 6) with malonic acid (535 mg, 5.12 mmole) as described in Example 2 gave 0.778 g (98%) of the title compound, mp (methanol) 71°–72° C. ν$_{max}$ (mull) 3140, 2600 (broad), 1680, 1630, 1465 cm$^{-1}$; δ(DMSO) 0.80 (3H, distorted t, terminal CH$_3$), 1.09–1.60 (18H, m, alkylene chain), 2.42 (2H, t, CH$_2$C≡C), 6.25 (1H, d, J 15.3 Hz, C=CH—CO$_2$H), 6.62 (1H, d, J 2 Hz, C-4H), 7.33 (1H, d, J 15.3 Hz, Ar CH=C), 7.79 (1H, d, J 2 Hz, C-5H).

M$^+$ 316.2042 (C$_{20}$H$_{28}$O$_3$ requires 316.2038).

EXAMPLE 8

5-(1-Octynyl)furan-2-carboxaldehyde

To a solution of 1-octyne (5.5 g, 50 mmole) in dry THF (40 ml) at −30° C. was added n-butyl lithium in hexane (1.05 eq). After warming to 0° C. over 1 hr a solution of zinc chloride (6.95 g, 50 mmole) in THF (50 ml) was added and temperature raised to room temperature over ½ hr. Sequentially, solutions of 5-bromofuran-2-carboxaldehyde (8.75 g, 50 mmole) in THF (20 ml) and tetrakis triphenylphosphinepalladium (0) (5.7 g, 10%) in THF (50 ml) were added. The mixture was heated to reflux for 2 hr after which it was cooled and added to dilute hydrochloric acid (50 ml). After extracting into diethyl ether (3×100 ml), drying the ethereal solution (MgSO$_4$) and removing the solvent under reduced pressure, the resulting oil was chromatographed on silica (DCM: Hexane 1:2) to give the title compound 6.83 g (67%) as an oil. ν$_{max}$ (film) 3150, 3125, 2225, 1680, 890, 770; δ(CDCl$_3$) 0.90(3H, distorted t), 1.42(8H, complex m), 2.45(2H, t, J=6.5 Hz), 6.60(1H, d, J=3.0 Hz), 9.65(1H, s).

EXAMPLE 9

(E-)3-[5-(1-Octynyl)-2-furanyl]prop-2-enoic acid

Reaction of 5-(1-octynyl)furan-2-carboxaldehyde (0.72 g, 3.5 mmole from example 8) with malonic acid (0.73 g, 7 mmole) as described in Example 2 gave 0.76 g (88%) of the title compound, mp(Hexane) 100°–100.5° C. ν$_{max}$ (mull) 2650 (broad), 1695, 1630, 1565, 1510, 1410, 1300, 1235, 1210 cm$^{-1}$; δ(CDCl$_3$) 0.90(3H, t, 6.8 Hz), 1.32(4H, m), 1.44(2H, m), 1.62(2H, m), 2.47(2H, t, J=6.5 Hz), 6.38(1H, d, J=15 Hz), 6.54(1H, d, J=3 Hz), 6.64(1H, d, J=3 Hz), 7.48(1H, d, J=15 Hz), 10.53 (1H, broad).

EXAMPLE 10

Diethyl 2-[5-(1-octynyl)-2-furanylmethylene]propan-1,3-dioate

Reaction of 5-(1-octynyl)furan-2-carboxaldehyde (1.6 g, 7.8 mmole from example 8) with diethylmalonate (1.25 g, 1.1 eq) as described in Example 3 gave, after chromatography on silica (DCM:Hexane 1:1), 2.17 g, (80%) of the title compound as an oil. ν$_{max}$ (mull) 3140, 2930, 2860, 2220, 1730, 1630, 1560, 1505, 1470, 1370, 1350, 1260, 1065, 1025, 800 cm$^{-1}$; δ(CDCl$_3$) 0.89(3H, distorted t) 1.41(14H, m), 2.41(2H, t, J=6.5 Hz), 4.30(2H, q, J=7.5 Hz), 4.41(2H, q, J=7.5 Hz), 6.57(1H, d, J=3 Hz), 6.73 (1H, d, J=3 Hz), 7.40(1H, s).

EXAMPLE 11

(Z)-2-[5-(1-octynyl)-2-furanylmethylene]propan-1,3-dioic acid monoethyl ester Diethyl 2-[5-(1-octynyl)-2-furanylmethylene]propan-1,3-dioate (1.04 g, 3 mmole from Example 10) was added to a solution of lithium hydroxide monohydrate (0.13 g, 1 eq) in THF/water (1:1, 15 ml) and the mixture was heated to 70° C. for 3 hr. The resulting clear solution was acidified and then extracted into diethyl ether (2×50 ml). The etheral solution was dried (MgSO$_4$) and the solvent removed under reduced pressure to give the title compound as a yellow solid which was recrystalised from hexane 0.65 g (68%), mp 89°–90° C., ν$_{max}$ (mull), 2600(broad), 2220, 1740, 1695, 1615, 1555, 1270, 1235, 1215 cm$^{-1}$; δ(CDCl$_3$), 0.89(3H, distorted t), 1.43(3H, t, J=7.5 Hz), 1.45(8H, m), 2.42 (2H, t, J=6.5 Hz), 4.40(2H, q, J=7.5 Hz), 6.54(1H, d, J=3.0 Hz), 6.86(1H, d, J=3.0 Hz), 7.57(1H, s), 11.5(1H, s).

EXAMPLE 12

Diethyl 2-[(Z)-5-(1-octenyl)-2-furanylmethylene]propan-1,3-)dioate

Diethyl 2-[5-(1-octynyl)-2-furanylmethylene]propan-1, 3-dioate (1.13 g, 3.25 mole from Example 10) in dry pyridine (25 ml) containing 5% palladium on barium sulphate (0.15 g) was hydrogenated at 1 atmosphere. After 1 hr the mixture had absorbed 1 equivalent of hydrogen and the catalyst was removed by filtration through celite. Removal of the solvent under reduced pressure followed by chromatography on silica (DCM: Hexane 2:1) gave the title compound 1.06 g (94%) as an oil, ν$_{max}$ (film) 3130, 2920, 2850, 1725, 1625, 1560, 1500, 1470, 1370, 1220 (broad), 1065, 1025, 800 cm$^{-1}$; δ(CDCl$_3$), 0.89(3H, distorted t), 1.30(6H, complex m), 1.32(3H, t, J=7.1 Hz), 1.36(3H, t, J=7.1 Hz), 1.46(2H, m), 2.39(2H, m), 4.28(2H, q, J=7.1 Hz), 4.38(2H, q, J=7.1 Hz), 5.74(1H, d, t, J$_d$=11.8 Hz, J$_t$=7.2 Hz), 6.16(1H, d, J=11.8 Hz), 6.38(1H, d, J=3.75 Hz), 6.79(1H, d, J=3.75 Hz), 7.42(1H, s).

EXAMPLE 13

(Z)-2-[(Z)-5-(1-octenyl)-2-furanylmethylene]propan-1,3-dioic acid, monoethyl ester Diethyl 2-[(Z)-5-(1-octenyl)-2-furanylmethylene]propan-1,3-dioate (0.8 g, 2.3 mmole from Example 12) was treated with lithium hydroxide monohydrate as described in Example 11 to give the title compound 0.7 g (96%) mp(Hexane) 91°–93° C., ν$_{max}$ (mull) 2600 (broad), 1740, 1690, 1670, 1610, 1550, 1420, 1275, 1210, 1190 cm$^{-1}$; δ(CDCl$_3$) 0.89(3H, t, J=6.5 Hz), 1.30(6H, m), 1.39(3H, t, J=7.2 Hz), 1.49(2H, m), 2.42(2H, m), 4.42(2H, q, J=7.2 Hz), 5.82(1H, d, t, J$_d$=11.8 Hz, J$_t$=7.2 Hz), 6.19 (1H, d, J=11.8 Hz), 6.44(1H, d, J=3.75 Hz), 7.01(1H, d, J=3.75 Hz), 7.71(1H, s), 11.05(1H, broad).

EXAMPLE 14

3-(1-Octynyl)furan-2-carboxaldehyde

Reaction of 3-bromofuran-2-carboxaldehyde (4.71 g, 27 mmole from Example 5) with 1-octyne (3 g, 27 mmole) as described in Example 8 afforded 3.96 g (72%) of the title compound, as an oil, after chromatography on silica (DCM:Hexane 1:2), $\nu_{max}$ (film) 2950, 2930, 2850, 2230, 1680, 1570, 1420, 1360, 1275, 890, 775 cm$^{-1}$; $\delta$(CDCl$_3$) 0.92(3H, distorted t), 1.42(8H, complex m), 2.48(2H, t, J=6.5 Hz), 6.59(1H, d, J=3 Hz), 7.62(1H, d, J=3 Hz), 9.82(1H, s).

EXAMPLE 15

(E)-3-[3-(1-Octynyl)-2-furanyl]prop-2-enoic acid

Reaction of 3-(1-octynyl)furan-2-carboxaldehyde (1.02 g, 5 mmole from example 14) with malonic acid (1.04 g, 10 mmole) as described in Example 2 gave 1.08 g (88%) of the title compound, mp (Hexane) 81°-81.5° C., $\nu_{max}$ (mull) 2600(broad), 1690, 1670(sh), 1620, 1410, 1320, 1270, 970, 890, 770 cm$^{-1}$; $\delta$(CDCl$_3$) 0.91(3H, t, J=6.9 Hz), 1.34(2H, m), 1.46(2H, m), 1.62(2H, m), 2.45(2H, t, J=7.0 Hz), 6.40(1H, d, J=15.9 Hz), 6.46(1H, d, J=1.8 Hz), 7.41(1H, d, J=1.8 Hz), 7.66(1H, d, J=15.9 Hz), 11.60(1H, broad).

EXAMPLE 16

Diethyl 2-[3-(1-octynyl)-2-furanylmethylene]propan-1,3-dioate

Reaction of 3-(1-octynyl)furan-2-carboxaldehyde (2.04 g, 10 mmole from Example 14) with diethyl malonate (1.98 g, 1.25 eq) as described in Example 3 gave, after chromatography on silica (DCM:Hexane 1:1) 1.96 (57%) of the title compound as an oil, $\nu_{max}$ (film) 2930, 2230, 1740, 1725, 1625, 1240, 1210, 1100 cm$^{-1}$; $\delta$(CDCl$_3$) 0.89(3H, distorted t), 1.32(3H, t, J=7.5 Hz), 1.35(3H, t, J=7.5 Hz), 1.40(8H, m), 2.40(2H, t, J=6.5 Hz), 4.28(2H, q, J=7.5 Hz), 4.36(2H, q, J=7.5 Hz), 6.45(1H, d, J=2 Hz), 7.40(1H, d, J=2 Hz), 7.60(1H, s).

EXAMPLE 17

(Z)-2-[3-(1-Ocytnyl)-2-furanylmethylene]propan-1,3-dioic acid, monoethyl ester

Diethyl 2-[3-(-octynyl)-2-furanyl]methylenepropan-1,3-dioate (1.04 g, 3 mmole from Example 16) was treated with lithium hydroxide monohydrate (0.14 g, 1.1 eq) as described in Example 11 to yield the title compound 0.69 g, (72%) mp (Hexane) 77°-77.5° C., $\nu_{max}$ (mull) 2600(vb), 1740, 1690, 1675, 1605, 1020, 900, 780, 755; $\delta$(CDCl$_3$) 0.87(3H, t, J=6 Hz), 1.35(3H, t, J=6 Hz), 1.4(8H, m), 2.43(2H, t, 6 Hz), 4.30(2H, q, J=6 Hz), 6.50(1H, d, J=2 Hz), 7.45(1H, d, J=2 Hz), 7.70(1H, s), 10.4(1H, bs).

EXAMPLE 18

Diethyl 2-[(Z)-3-(1-Octenyl)-2-furanylmethylene]propan-1,3-dioate

Diethyl 2-[3-(1-octynyl)-2-furanylmethylene]propan-1,3-dioate(1.04 g, 3 mmole from example 16) was hydrogenated over 5% palladium on barium sulphate as described in Example 12 to yield, after chromatography on silica (DCM:Hexane 1:1) the title compound 0.84 g (80%) as an oil, $\nu_{max}$ (film) 1740, 1720, 1610, 1025, 885, 865, 760; $\delta$(CDCl$_3$) 0.88(3H, distorted t), 1.32(3H, t, J=7 Hz), 1.34(8H, m), 1.37(3H, t, H=7 Hz), 2.26(2H, m), 4.28(2H, q, J=7 Hz), 4.40(2H, q, J=7 Hz), 5.8(1H, m), 6.33(1H, m), 6.6(1H, d, J=2 Hz), 7.45(1H, d, J=2 Hz), 7.49(1H, s).

EXAMPLE 19

(Z)-2-[(Z)-3-(1-Octenyl)-2-furanylmethylene]propan-1,3-dioic acid, monoethyl ester Diethyl 2-[(Z)-3-(1-octenyl)-2-furanyl]methylene propan-1,3-dioate(0.65 g, 1.87 mmole, from Example 18) was treated with lithium hydroxide mono hydrate (0.85 g 1.1 eq) as described in Example 11 to yield the title compound 0.45 g (75%) mp (Hexane) 97°-99° C., $\nu_{max}$ (mull) 2550 (broad), 1735, 1685, 1670, 1600, 1420, 1260, 1220 cm$^{-1}$ $\delta$(CDCl$_3$) 0.88(3H, distorted t), 1.37(8H, m), 1.37(3H, t, J=7.2 Hz), 2.27(2H, m), 4.41(2H, q, J=7.2 Hz), 5.83(1H, d, t, J$_d$=11.5 Hz, J$_t$=7.4 Hz), 6.32(1H, d, J=11.5 Hz), 6.61(1H, d, J=1.9 Hz), 7.50(1H, d, J=1.9 Hz), 7.62(1H, s).

EXAMPLE 20

5-(1-Octynyl)thiophene-2-carboxaldehyde

5-Bromo-2-thiophenecarboxaldehyde (8.5 g, 0.05 mole) was combined with 1-octyne (11.0 g, 0.1 mole) and triethylamine (200 ml). The mixture was degassed under argon and cuprous iodide (950 mg, 10 mole %) and tetrakis (triphenylphosphine) palladium (1.75 g, 5 mole %) were added. The mixture was heated at 105° C. for twenty hours under argon and cooled. The triethylamine was evaporated and the residue purified by chromatography on silica eluting with hexane/chloroform (3:1) to yield the title compound 8.6 g (83.7%) as a yellow oil. mp 130° C., $\nu_{max}$ (film) 3320, 2225, 1675, 1050, 805, 780, 675; $\delta$(CDCl$_3$) 0.87(3H, t, J=6 Hz), 1.33(8H, m), 2.33(2H, t, J=6 Hz), 7.13(1H, d, J=6 Hz), 7.65(1H, d, J=6 Hz), 9.87(1H, s).

M+ 220.0919 C$_{13}$H$_{16}$OS requires 220.0922.

EXAMPLE 21

(E)-3-[5-(1-Octynyl)-2-thienyl]prop-2-enoic acid

Reaction of 5-(1-octynyl)-2-thiophene carboxaldehyde (880 mg, 4 mmole) with malonic acid as described in Example 2 yielded 0.98 g (93.5%) of the title compound after recrystallization from hexane mp 79° C.; $\nu_{max}$ (mull) 2600 (broad), 1690, 1670, 1610, 940, 845, 800; $\delta$(CDCl$_3$) 0.90(3H, t, J=6 Hz), 1.50(8H, m), 2.40(2H, t, J=6 Hz), 6.15(1H, d, J=15 Hz), 7.05(1H, d, J=4.5 Hz), 7.13(1H, d, J=4.5 Hz), 7.85(1H, d, J=15 Hz), 11.3(1H, bs). M+ 262.1022 C$_{15}$H$_{15}$O$_2$S requires 262.1027. Found; C, 68.96; H, 7.14; C$_{15}$H$_{15}$O$_2$S requires; C, 68.68; H, 6.92.

EXAMPLE 22

Diethyl 2-[5-(1-octynyl)-2-thienylmethylene]propan-1,3-dioate

Reaction of 5-(1-octynyl)-2-thiophenecarboxaldehyde (2.64 g 12 mmole) with diethyl malonate as described in Example 3 yielded the title compound as a yellow oil 4.2 g (96.7%). $\nu_{max}$(film) 2225, 1730, 1615, 865, 805; $\delta$(CDCl$_3$), 0.90(3H, t, J=6 Hz), 1.5(14H, m), 2.32(2H, t, J=6 Hz), 4.30(2H, q, J=7.5), 4.4(2H, q, J=7.5), 7.03 (1H, d, J=3 Hz), 7.23(1H, d, J=3 Hz), 7.76(1H, s).

Found; C, 64.72; H, 6.52; C$_{20}$H$_{26}$O$_4$S requires; C, 64.65; H, 6.63.

EXAMPLE 23

(Z)-2-[5-(1-Octynyl)-2-thienylmethylene]propan-1,3-dioic acid, monoethyl ester

Hydrolysis of diethyl 2-[5-(1-octynyl)-2-thiophenylmethylene]propan-1,3-dioate (724 mg, 2 mmole) by the method described in Example 11 yielded the title compound as a pale yellow solid 650 mg 92% mp (96°-7°) (Hexane) $\nu_{max}$(mull) 2225, 1730, 1690, 1670, 1605, 1080, 820, 730; $\delta$(CDCl$_3$) H$^1$: 0.87(3H, t, J=6 Hz), 1.33(3H, t, J=7.5), 1.4(8H, m), 2.43(2H, q, J=7.5 Hz), 7.07(1H, d, J=4.5 Hz), 7.93(1H, d, J=4.5 Hz), 8.20(1H, s), 11.23(1H, bs).

C$^{13}$: 168.5, 166.8, 140.4, 138.7, 135.6, 133.9, 131.3, 117.3, 100.6, 73.7, 62.5, 31.3, 28.5, 28.3, 22.6, 20.00, 14.2, 14.1.

Partial C$^{13}$-H$^1$ coupled: 168.56, 168.46, 166.96, 166.90, 166,86, 166.79, 166.73, 166.69.

EXAMPLE 24

2-[5-(1-Octynyl)-2-thiophenylmethylene]propan-1,3-dioic acid

Hydrolysis of the corresponding diethyl ester (724 mg 2 mmole) as described in example 4 yielded the title compound as yellow solid 265 mg 43.3% mp 106°; $\nu_{max}$ (mull) 2225, 1730, 1630, 1085, 810, 740; $\delta$(CDCl$_3$) 0.90(3H, t, J=6 Hz), 1.37(8H, m), 2.47(2H, t, J=6 Hz), 7.17(1H, t, d, J=6 Hz), 7.63(1H, d, J=6 Hz), 8.60 (1H, s), Found; C, 62.33, H, 5.80, C$_{16}$H$_{18}$O$_4$S requires; C, 62.72; H, 5.92.

EXAMPLE 25

4-(1-Octynyl)thiophene-2-carboxaldehyde

Reaction of 4-bromo-2-thiophenecarboxaldehyde (3.40 g 2 mmole, prepared by the methods described by D. Chadwick et al, J.C.S. Per 1 1766, 1973), with 1-octyne (4.40 g, 4 mmole) as described in Example 20 gave the title compound as a yellow oil (89.0%); mp 2° C.; $\nu_{max}$ 3100, 2260, 1685, 1160, 855, 655, 622; $\delta$H(CDCl$_3$) 0.88(3H, t, J=6 Hz), 1.3(8H, m), 2.33(2H, t, J=6 Hz), 7.7(2H, s), 9.9 (1H, s).

EXAMPLE 26

(E)-3-[4-(1-Octynyl)-2-thienyl]prop-2-enoic acid

Reaction of 4-(1-octynyl)-2-thiophenecarboxaldehyde (1.1 g, 5 mmole) with malonic acid by the method described in Example 2 yielded the title compound 1.19 g, (91%) as a fawn solid, mp 81° (hexane) $\nu_{max}$ (mull) 2600(vb) 1695, 1680, 1625, 965, 940, 830, 760; $\delta$(CDCl$_3$) 0.90(3H, t, J=6 Hz), 1.4(8H, m), 2.37(t, 2H, J=6 Hz), 6.22(H, d, 15 Hz), 7.25(1H, s), 7.40(1H, s), 7.80(d, 1H, J=15 Hz), 11.5(1H, bs).

Found; C, 68.39; H, 6.70; C$_{15}$H$_{18}$O$_2$S requires; C, 68.68; H, 6.92.

EXAMPLE 27

3-Bromo-4-(1-octynyl)thiophene

This was prepared by the method of Example 20. The title compound was obtained as a yellow oil 4.90 g (87.5%) from 3,4-dibromothiophene (5.0 g, 20.7 mmole) $\nu_{max}$ (film) 3120, 2225, 850, 790, 780; $\delta$(CDCl$_3$), 0.90(3H, t, J=6 Hz), 1.33(8H, m), 2.30(2H, t, J=6 Hz), 7.20(1H, d, J=4.5 Hz), 7.35(1H, d, J=4.5 Hz).

EXAMPLE 28

4-(1-Octynyl)thiophene-3-carboxaldehyde

3-Bromo-4-(1-octynyl)thiophene (2.0 g, 7.38 mM) was dissolved in dry tetrahydrofuran under argon. Butyl lithium (2.85 ml of a 2.6M hexane solution) was added keeping the temperature at −20° C. After 30 min at this temperature, N,N-dimethl formamide (2 ml) was added and the mixture allowed to attain room temperature overnight. Hydrolysis and extraction with ether yielded a yellow oil (1.70 g) which was purified by chromatography on silica eluting with chloroform/hexane (1:1). This gave 550 mg (34%) of the title compound as a yellow oil. $\nu_{max}$(film) 3100, 2225, 1680, 880, 760, 670; $\delta$(CDCl$_3$) 0.93(3H, t, J=6 Hz), 1.3(8H, m), 2.2(2H, t, 6 Hz), 7.25(1H, s), 7.67(1H, s), 9.93(1H, s).

EXAMPLE 29

(E)-3-[4-(1-Octynyl)-3-thienyl]prop-2-enoic acid

Reaction of 4-(octynyl)-3-thiophenecarboxaldehyde (550 mg, 2.5 mmole) with malonic acid by the method described in Example 2 yielded the title compound 272 mg (41.5%) mp °C.; $\nu_{max}$ (mull) 2600(vb), 1790, 1615, 940, 865, 835, 760; $\delta$(CDCl$_3$) 0.90(3H, distorted t), 1.40(8H, m), 2.37(2H, t, J=6 Hz), 6.23(1H, d, J=16 Hz), 7.22(1H, bs), 7.37(1H, bs), 7.77(1H, d, J=16 Hz), 10.3(1H, bs).

EXAMPLE 30

3-Bromo-2-(1-octynyl)thiophene 2,3-Dibromothiophene (3.78 g 15.6 mmole) was reacted with 1-octyne (2.57 g 23.4 mmole) using the method given in Example 20. The reaction product was purified by chromatography on silica eluting with hexane to yield 3.70 g (87.2%) of the title compound as a yellow oil bp 0.05 155°, $\nu_{max}$ (mull) 3100, 2225, 870, 710; $\delta$(CDCl$_3$), 0.9(3H, t, J=6 Hz), 1.3(8H, m), 2.47(2H, t, J=6 Hz), 6.9(d, 1H, J=9 Hz), 7.13(1H, d, J=9 Hz).

EXAMPLE 31

2-(1-Octynyl)-3-thiophenecarboxaldehyde

Conversion of 3-bromo-2-(1-octynyl)thiophene (542 mg, 2 mM) to the title compound was achieved by the procedure of Example 28. Yield 249 mg (56.6%) $\nu_{max}$ (film) 2225, 1675, 870, 710 $\delta$(CDCl$_3$) 0.90(3H, t, J=6 Hz), 1.3(8H, m), 2.45(2H, t, J-6 Hz), 6.90(d, 1H, J=9 Hz), 7.10(1H, d, J=9 Hz), 9.90(1H, s).

EXAMPLE 32

3-[2-(1-Octynyl]-3-thiophene]prop-2-enoic acid

Reaction of 2-(1-octynyl)-3-thiophenecarboxaldehyde (549 mg, 2.5 mmole) with malonic acid by the method described in Example 2 yielded the title compound 596 mg (91%) mp °C.: $\nu_{max}$ (mull) 2700(vb), 2225, 1690, 1620, 970, 940, 805 $\delta$(CDCl$_3$) 0.90(3H, t, J=6 Hz), 1.3(8H, m), 2.43(2H, t, J=6 Hz), 6.13(1H, d, J=16 Hz), 7.00(1H, d, J=4.5 Hz), 7.10(1H, d, J=4.5 Hz), 7.75(1H, d, J=16 Hz).

PHARMACOLOGICAL DATA (1) RBL-1 5-Lipoxygenase Screen

5-Lipoxygenase enzyme was prepared as a 10,000 g supernatant from RBL-1 cells by the method of Jakschik (Jakschik, B. A., F. F. Sun, L. M. Lee, and M. M. Steinhoff, 1980, Biochem. Biophys. Res. Comm. 95, 103). The 10,000 g supernatant was diluted with homogenization buffer to the equivalent of 1.5–2.5 × 10⁷ cells. ml.⁻¹ and made 2 mM with respect to CaCl₂. Aliquots of 0.5 ml were then dispensed into tubes, and incubated at 29° C. with 5 ul ethanol or compound in ethanol at the desired concentration for 2 min. Then [1-¹⁴C] arachidonic acid was added in buffer to give a final concentration of 6.3 uM and 0.2 uCi per incubation, and the reaction continued at 29° C. for 2 min. The reaction was terminated by adding 1 ml of acetone and cooling on ice, 0.5 ml of ice-cold saline and 100 ul of 2N formic acid were added, and the mixture was extracted with 2×2 ml of chloroform. The extract was stored under N₂ at −20° C. until analysis by chromatography. Activity was measured as the percentage of total radioactivity found in 5-HETE and 5,12-diHETE, and inhibition calculated as the decrease in formation of the sum of these two species in compound-treated incubates relative to control incubations.

(2) Cyclo-oxygenase Screen

The inhibition of cyclo-oxygenase was measured in a buffered incubation (0.2M Tris-HCl, pH 8.0, containing 1 mM ethylene diaminetetraacetic acid) comprising 0.96 mg lyophilised bovine seminal vesicle microsomes, 5–15 μM arachidonic acid containing 0.2 μCi [1-¹⁴C] arachidonic acid, 2 mM reduced glutathione, 0.5 mM hydroquinone, 1 μM haemoglobin and compound (0–0.05 mM in 5 μl dimethylsulphoxide or absolute ethanol) in a total volume of 2.0 ml. Compounds were preincubated with the incubation constitutents for 5 min at 37° C. before the reaction was started by the addition of the arachidonic acid. The reaction was continued at 37° C. for 2 min, then stopped by placing the incubations on ice and the addition of 1.2 ml 0.2M citric acid. Unmetabolised substrate and prostaglandin products were extracted in ethyl acetate (2×4 ml), the combined extracts washed with 0.8 ml water, and separated by thin-layer chromatography (Kieselgel GF₂₅₄ plates in ethyl acetate:acetone:glacial acetic acid, 90:10:1, v/v). Recovery was 65–80%. The regions on the thin-layer chromatography plate that chromatographed with authentic arachidonic acid or prostaglandins E₂ and F₂α (R_f's 0.70, 0.28 and 0.16 respectively) were scraped and the radioactivity in each determined by liquid scintillation counting with a correction for quenching being made by the external standard-channels ratio method. Inhibition of cyclo-oxygenase activity was calculated from the decrease in prostaglandin formation. Each compound concentration was tested in triplicate and the 50% inhibitory concentration, if determined, was calculated by linear regression from the inhibitory data at, at least three different compound concentrations.

BIOLOGICAL RESULTS

| Example | Per cent inhibition of 5-lipoxygenase at X μM concentration | Per cent inhibition of cyclo-oxygenase at 50 μM concentration |
|---|---|---|
| 2 | 30% at 20 μM | |
| 4 | 72% at 20 μM | 15% |
| 7 | 38% at 5 μM | 46% |

I claim:
1. A compound of the formula

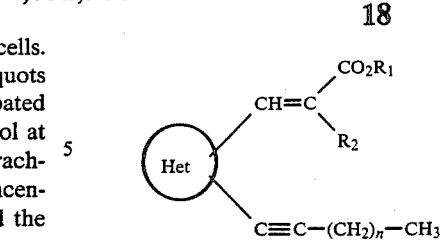

wherein
$R_1$ is hydrogen or $C_1$–$C_6$ alkyl;
$R_2$ is hydrogen;
n is an integer of from 2 to 12;

represents pyridyl, thienyl or furyl or a pharmaceutically acceptable salt thereof.

2. A compound according to claim 1, in which n is an integer of from 4 to 12.

3. A compound according to claim 1 in the form of a pharmaceutically acceptable salt.

4. A compound according to claim 1 which is selected from the group consisting of:
(E)3-[3-(1-tridecynyl)-4-pyridyl]prop-2-enoic acid;
(E)3-[3-(1-tridecynyl)-2-furanyl]prop-2-enoic acid;
(E)-3-[5-(1-Octynyl)-2-furanyl]prop-2-enoic acid;
(E)-3-[3-(1-Octynyl)-2-furanyl]prop-2-enoic acid;
(E)-3-[5-(1-Octynyl)-2-thienyl]prop-2-enoic acid;
(E)-3-[4-(1-Octynyl)-2-thienyl]prop-2-enoic acid;
(E)-3-[4-(1-Octynyl)-3-thienyl]prop-2-enoic acid;
3-[2-(1-Octynyl]-3-thiophene]prop-2-enoic acid; or a pharmaceutically acceptable salt or $C_{1-6}$ alkyl ester thereof.

5. A compound according to claim 1, wherein

is substituted in the 1,2 or 1,3 positions.

6. A compound according to claim 1, wherein

is substituted in the 1,2, positions.

7. A compound according to claim 1, wherein

is furyl.

8. A compound 3-[3-(1-tridecynyl)-2-furanyl]prop-2-enoic acid or a pharmaceutically acceptable salt thereof.

9. A pharmaceutical composition for treatment of allergic disorders comprising an effective amount of a compound according to claim 1 or a pharmaceutically acceptable salt thereof, and a pharmaceutically acceptable carrier.

10. A method of treating allergic disorders in mammals which comprises administering to the sufferer an effective non-toxic amount of a compound according to claim 1 or a pharmaceutically acceptable salt thereof.

11. A pharmaceutical composition for treatment of inflammatory disorders comprising an effective amount of a compound according to claim 1 or a pharmaceutically acceptable salt thereof, and a pharmaceutically acceptable carrier.

12. A method of treating inflammatory disorders in mammals which comprises administering to the sufferer an effective non-toxic amount of a compound according to claim 1 or a pharmaceutically acceptable salt thereof.

* * * * *